(12) United States Patent
Jay

(10) Patent No.: US 7,175,617 B2
(45) Date of Patent: Feb. 13, 2007

(54) HAIR TREATMENT METHOD

(76) Inventor: Harvey H. Jay, 14 Cayuga Rd., Scarsdale, NY (US) 10583

( * ) Notice: Subject to any disclaimer, the term of this patent is extended or adjusted under 35 U.S.C. 154(b) by 33 days.

(21) Appl. No.: 10/418,604

(22) Filed: Apr. 18, 2003

(65) Prior Publication Data

US 2004/0092917 A1 May 13, 2004

Related U.S. Application Data

(63) Continuation of application No. 10/291,086, filed on Nov. 8, 2002, now Pat. No. 6,824,542.

(51) Int. Cl.
*A61B 18/18* (2006.01)

(52) U.S. Cl. .................. 606/9; 606/3; 606/10; 607/88; 128/898

(58) Field of Classification Search .................... 606/3, 606/9–13, 16–20, 22–26; 607/88–91; 128/898
See application file for complete search history.

(56) References Cited

U.S. PATENT DOCUMENTS

| | | | |
|---|---|---|---|
| 5,425,728 A | 6/1995 | Tankovich | |
| 5,595,568 A | 1/1997 | Anderson et al. | |
| 5,683,380 A | 11/1997 | Eckhouse et al. | |
| 5,735,844 A * | 4/1998 | Anderson et al. | 606/9 |
| 5,849,029 A | 12/1998 | Eckhouse et al. | |
| 5,885,273 A | 3/1999 | Eckhouse | |
| 5,895,568 A | 4/1999 | Koltunov | |
| 6,050,990 A | 4/2000 | Tankovich et al. | |
| 6,063,076 A | 5/2000 | Mehl, Sr. et al. | |
| 6,152,917 A | 11/2000 | Tankovich | |
| 6,162,211 A | 12/2000 | Tankovich et al. | |
| 6,162,212 A | 12/2000 | Kreindel et al. | |
| 6,174,325 B1 | 1/2001 | Eckhouse | |
| 6,228,074 B1 * | 5/2001 | Almeida | 606/9 |
| 6,267,771 B1 | 7/2001 | Tankovich et al. | |
| 6,280,438 B1 | 8/2001 | Eckhouse et al. | |
| 6,383,176 B1 | 5/2002 | Connors et al. | |
| 6,387,089 B1 | 5/2002 | Kreindel et al. | |
| 6,406,474 B1 | 6/2002 | Neuberger et al. | |
| 6,676,655 B2 | 1/2004 | McDaniel | |

* cited by examiner

*Primary Examiner*—A. Farah
(74) *Attorney, Agent, or Firm*—R. Neil Sudol; Henry D. Coleman; William J. Sapone

(57) ABSTRACT

A hand held device generates a predetermined number of pulses of light having a predetermined electromagnetic spectrum, a predetermined duration, a predetermined inter-pulse interval, and a predetermined total energy. The pulse sequence is delivered to a skin surface to temporarily remove hair. A period of time for reappearance of hair on the selected skin surface after the using of the device to remove hair from the selected skin surface is determined by counting the days to hair reappearance after a test light application. Subsequently, the device is used periodically to apply the pulses of light to the selected skin surface at intervals of shorter length than the determined period of hair regeneration, thereby temporarily maintaining the selected skin surface free of visible hair.

32 Claims, 1 Drawing Sheet

HAIR TREATMENT METHOD

CROSS-REFERENCE TO RELATED APPLICATION

This application is a continuation-in-part of application Ser. No. 10/291,086 filed Nov. 8, 2002, now U.S. Pat. No. 6,824,542.

BACKGROUND OF THE INVENTION

This invention relates generally to a hair treatment process. More particularly, this invention relates to a method for the temporary removal of hair and for the retardation of hair growth.

As discussed in U.S. Pat. No. 6,280,438, hair may be removed from selected skin surfaces by the application of intense, wide area, pulsed electromagnetic (light) energy. According to the methodology of U.S. Pat. No. 6,280,438, the energy heats the hair and coagulates the tissue around the hair and follicle without damaging the healthy skin. Pursuant to that prior art disclosure, it is preferable to provide an optically transparent water based gel on the skin prior to treatment with the electromagnetic energy. The gel cools the epidermis but is applied so as not to enter the cavity around the hair follicle, and thus does not cool the hair and the hair follicle. The applied energy then coagulates the hair without damaging the skin.

U.S. Pat. No. 6,280,438 teaches the use of incoherent polychromatic radiation in a wavelength range that penetrates into the skin without being highly attenuated. It is indicated in the patent that wavelengths shorter than 550 nm are not useful because they will be highly attenuated before reaching the lower parts of the hair follicles. Instead, wavelengths in the range of 550 to 630 nm are heavily absorbed by blood and can therefore be used to coagulate the vessels that feed the hairs. Additionally, longer wavelengths, in the range of 600 to 1100 nm have a very good penetration into non-pigmented skin and can be used to couple to the melanin of the hair.

U.S. Pat. No. 5,885,273 discloses a method of removing hair that includes producing a plurality of pulses of incoherent electromagnetic energy, which is filtered in accordance with the color of the hair being removed. A flashlamp produces pulses having delays on the order of 0.1 msec to 100 msec, and an energy fluence on the order of 10 to 100 $J/cm^2$. Energy that has a wavelength of less than 500 nm or 600 nm and greater than 1300 nm is preferably filtered out. Light is applied to the treated area in either a long pulse or in a sequence of pulses separated by a delay. The delay and/or pulse length is preferably controlled by the operator to provide enough heat to remove the hair but not enough heat to damage the skin. For example, the pulse length or delay between the pulses should be more than the cooling time of the gel covered epidermis and less than the cooling time of the hair and follicle. Specifically, a pulse length of 50 msec if a single pulse is used or a delay of 50 msec between the pulses if a pulse sequence is used are appropriate values.

In brief, the art using electromagnetic radiation such as pulses of incoherent light is intended to permanently remove hair from selected skin surfaces. The light pulses have parameters such as spectral dispersion, pulse duration and total energy that are selected to destroy the hair follicles in the selected skin area. Understandably, such methods carry a certain amount of risk that the skin may be damaged. Accordingly, the prior art methods of hair depilation are typically intended for use by trained cosmetologists and other professionals. The consuming public is left with few options in removing undesired hair.

OBJECTS OF THE INVENTION

An object of the present invention is to provide a method for treating hair to at least retard hair growth.

It is a related object of the present invention to provide a method for temporary hair removal.

A more particular object of the present invention is to provide such a method of hair treatment or removal that is safe for home use.

It is a related object of the invention to provide a method for hair treatment, which may replace current home-based methods, for instance, of shaving, waxing, plucking, tweezing, or using depilatories.

A further object of the present invention is to provide such a treatment method that can result in a smooth cleaner hair removal than is possible with razors and shavers.

These and other objects of the present invention will be apparent from the drawings and descriptions herein. It is to be understood that each object of the invention is achieved by at least one embodiment of the invention. It is not necessarily the case that any embodiment achieves all of the objects of the invention.

SUMMARY OF THE INVENTION

A hair treatment method comprises, in accordance with the present invention, generating a predetermined number of pulses of light each having a predetermined electromagnetic spectrum, and directing the pulses of light towards a skin surface. The light pulses having at least one pulse duration, at least one inter-pulse interval (if the number of pulses is greater than one), and a total energy all predetermined to at least temporarily retard growth of hair along the skin surface. After lapse of a period of time after the directing of the pulses towards the skin surface, the predetermined number of pulses of light are again generated and directed towards the skin surface.

The pulse parameters, namely, the pulse number, the pulse duration(s), the inter-pulse interval(s), the total energy and the spectral distribution(s), are selected in concert to only retard the growth of hair and/or to temporarily prevent the appearance of hair on the treated skin surface. Thus, in contrast to prior methods, which are aimed at completely destroying the hair follicle and terminating hair growth, the present method contemplates only a partial destruction of the follicles or, alternatively, a destruction of the hair inside the follicles. In either case, the hair will grow and again appear on the treated surface in the absence of additional controlled light application. However, the rate at which the hair grows will be reduced by virtue of the application of electromagnetic radiation pursuant to the present invention.

The light used in a hair treatment method in accordance with the present invention may be incoherent and produced by a flashlamp or other source of incoherent electromagnetic radiation. Alternatively, the light may be coherent and produced by a laser source. In the former case the electromagnetic spectrum of the light pulses is a band of wavelengths, while in the latter case, the electromagnetic spectrum of a light pulse delivered at one time is a single wavelength. In the former case filters may be used to limit the band of transmitted wavelengths, while in the latter case the laser source may be adjustable or tunable for producing wavelengths of different frequencies.

In accordance with the present invention, a user determines the time it takes for the hair to regenerate and reappear on the treated skin surface and reapplies the light pulses prior to the expected time of hair growth through the treated skin surface. Owing to a hair growth rate that may decrease with continuing application of light energy, the user need reapply the light pulses at an increasing interval. More specifically, a hair removal method in accordance with the present invention includes generating a predetermined number of pulses of light each having a predetermined electromagnetic spectrum and applying the pulses of light to a given skin surface, the pulses having at least one predetermined pulse duration, at least one predetermined inter-pulse interval (if the number of pulses is greater than one), and a predetermined total energy. The various pulse parameters are "predetermined" insofar as they are set or selected prior to the application of the light energy to the selected skin surface. The determination of the different pulse parameters is generally made partially at the time of manufacture of the light-generating device and partially by the selection or selections made by the user. At least in part owing to the application of the pulses to the skin surface, an appearance of visible hair fibers on the skin surface is temporarily prevented. Passing days are then counted between the applying of the pulses to the skin surface and a subsequent reappearance of hair fibers on the skin surface, thereby determining an expected hair regeneration period. After determination of this hair regeneration period, the same pulse sequence is generated, having the same pulse number, the same electromagnetic spectrum(s), the same pulse duration(s), the same inter-pulse interval(s) (if applicable), and the same total energy. This pulse sequence is directed towards the given skin surface. Thereafter, prior to a lapse of the determined hair regeneration period, the light application is repeated with pulses of light having (if desired) the same spectrum, the same number, the same duration, the same inter-pulse interval (if applicable), and the same total energy. It is to be noted that the hair regeneration period may lengthen with time, in part as a result of the light treatments. In recognition of that potentiality, the regeneration time may be recalculated after any given number of treatments. And if the regeneration time does increase, the interval between successive light treatments may be increased accordingly.

The present invention is thus directed to a method for the temporary removal of hair wherein light application is repeated prior to hair reappearance. This method serves to maintain a smooth and hair free skin surface continuously as long as the light application is repeated in due course prior to the expected time of hair reappearance.

The method of the present invention contemplates a gradual reduction in the frequency of light treatment, owing to a diminution in the hair growth rate. In an example, a user may initially be required to apply the pulsed light energy at intervals of one week in order to prevent the reappearance of hair on the treated hair surface. After several weeks or months of periodic light treatment, this rate of light energy application may be reduced to biweekly or monthly applications. The initial period of hair reappearance, as well as the rate of hair growth retardation, will be determined by the individual's genetics as to skin color, hair color, hair thickness, hair density, etc., and by the selected treatment parameters such as total energy, pulse rate, pulse duration, light spectrum, etc., as well as by the particular area on the user's body. In any given individual, the growth rates of hair on the face, underarms, legs, etc., vary. In addition, the change in hair growth rate using the present methodology may differ from body area to body area. The light treatment method of the present invention also affects hair parameters other than growth rate. Again depending on the individual's genetics, the location of the hair treated, and the selected treatment parameters, the user's hair may experience changes in thickness, density, and color. More specifically, in many individuals, hair is likely to become finer, less dense, and lighter in color.

The method of the present invention may be applied to facial hair, leg hair, underarm hair, chest hair, etc., using hand held devices of prior art designs, for instance, with a light source such as a flashlamp, a reflector, one or more lenses, and an application interface such as a skin-contacting crystal. The crystal may function as a cooling element. Alternatively, a separate cooling medium such as a gel may be applied to the skin surface prior to the light application.

Accordingly, the present invention contemplates the use of a hand held device for generating a predetermined number of pulses of light having a predetermined electromagnetic spectrum and for applying the pulses of light to a skin surface, the pulses having one or more predetermined durations, one or more predetermined inter-pulse intervals (if number of pulses is greater than one), and a predetermined total energy. The device is used to temporarily remove hair from a selected skin surface and will in many cases retard the rate of hair growth. A period of time for reappearance of hair on the selected skin surface after the using of the device to remove hair from the selected skin surface is determined, for instance, by simply counting the days to hair reappearance after a test light application. Subsequently, the device is used periodically to apply the pulses of light to the selected skin surface at intervals of shorter length than the determined period of hair regeneration, thereby temporarily maintaining the selected skin surface free of visible hair. The regeneration time after any number of treatments may be measured again after any number of light treatment sessions. If the regeneration time is increased (owing to hair growth retardation), the interval between successive light treatments may be increased accordingly.

The inter-pulse interval (where the number of pulses is greater than one) may, in different applications of the invention, be anywhere from 1 millisecond to 2 seconds. Generally, the smaller the inter-pulse interval, the greater the risk of damage to the skin. Thus, the smaller inter-pulse intervals should be used only in professional settings. In home-based embodiments of the invention, the inter-pulse interval of a light treatment is preferably greater than 200 msec. An inter-pulse interval of such a magnitude allows partial cooling of the hair follicles and reduces the chances of complete follicle destruction and inadvertent damage to the epidermis. Preferably, the inter-pulse interval is between 200 msec and about 500 msec. An inter-pulse interval of 300 msec is effective.

The total energy applied may be anywhere from 1 Joule per square centimeter of treated skin surface to about 200 $J/cm^2$. Generally, the higher energies entail greater risk to skin integrity and should be used only by skilled professionals. For home use, the total energy applied should be lower, between approximately 5 $J/cm^2$ and approximately 40 $J/cm^2$ of the skin surface. This energy range is appropriate for persons of light skin color. Where the skin color is on the dark side, the upper limit of the total energy applied to a unit of skin surface should be less, for instance, approximately 20 $J/cm^2$.

Generally, it is contemplated that devices used in a method pursuant to the present invention will require a selection of a maximum or total energy to be applied to a skin surface. This requirement typically entails some restriction on the user's freedom in selecting the magnitudes of other pulse parameters. In a simple device, the user may be able to select only one pulse parameter, namely the total energy. Such a device might, for instance, have high, medium and low settings. In a more complex device, setting of the total energy applied by a pulse sequence will limit the range of options available to the user in setting the other parameters. For instance, once the user selects the total energy and the pulse duration, the number of pulses is determined, provided that the rate of energy production or intensity is not adjustable. If the intensity is adjustable, the user will have some leeway in selecting both the pulse duration and the number of pulses. In that case, the intensity may be automatically controlled by the light-generating device so that the total energy does not exceed the set value.

The duration of the light bursts or pulses may be as little as 1 millisecond or as great as two seconds. The shortest durations and higher energies are recommended for professionally supervised light treatments only. For ordinary consumers or unskilled users, the pulse duration should be longer, preferably above approximately 6 msec and more preferably between approximately 6 msec and approximately 20 msec. A pulse duration of 7 msec is effective.

Pursuant to one embodiment of the present invention, the light of the pulses is incoherent and the spectrum includes wavelengths between about 300 nm and 1200 nm. Longer wavelengths are used for darker skin, for deeper hairs and deeper removal. In some embodiments of the invention, the spectrum of the pulses may be limited to wavelengths between about 300 nm and 550 nm. These embodiments will require a more frequent application of the light energy to effectuate temporary hair removal. However, because of the retardation of hair growth, the frequency of light application required to maintain a hair free skin surface will generally decrease with use.

The number of pulses in each pulse sequence or treatment session (as applied to a given skin area) may be between one and ten, while the total duration of a pulse sequence ranges between 1 millisecond and 38 seconds.

As indicated above, the present invention contemplates that some adjustment may be made by the user in the particular operational parameters of the light application device. For instance, a simple hand-held device may have a plurality of settings, for instance, high, medium, and low, where one or more of the operational parameters have different pre-established values depending on the setting. Thus, high, medium, and low settings may vary in the number of applied pulses, the pulse duration, the inter-pulse interval, and/or the total energy applied. A user could start with a low setting to see whether the hair falls out and if not, try the next higher setting. Usually, it is preferable to use the lowest setting which accomplishes the desired result.

It is to be noted that consumer devices may be preprogrammed with automatically operating safety controls which inhibit the user from inadvertently exposing himself or herself to dangerous quantities of light energy. Thus, in a relatively complex consumer product, the user's setting of one parameter at a potentially dangerous value will cause the device either to limit the selectable ranges of one or more other pulse parameters or to automatically adjust pulse parameters to prevent an excessive rate of energy delivery. For instance, the selection of a small inter-pulse interval may prevent the user from selecting a long pulse duration and/or a small number of pulses or, alternatively, may result in an automatic diminution of the intensity (e.g., via engagement of an intensity-reducing filter).

The present invention provides a method for the temporary removal of hair. The method is safe for home use. The energies used are sufficiently low to avoid skin damage. Because the light is applied prior to the appearance of hair on a skin surface, the skin surface may be maintained in a hairless condition continuously. If the individual wishes to grow hair at any location, this is possible by merely refraining from light application. The present invention contemplates the use of a light applicator periodically, say, at intervals of a week to a few months. In some cases, the light application may be daily, as a substitute for daily shaving with a razor or shaver.

In contrast to shaving, which cuts hairs at or above the skin surface, the method of present invention severs the hairs below the skin surface, thereby presenting a smoother, cleaner, more complete hair removal. In contrast, all conventional methods of hair removal, including shaving, waxing, plucking, tweezing, electrolysis, laser light application, incoherent light application, or the use of depilatories, require the protrusion of the hairs at the skin surface.

It should be understood that the present methodology may be used in professional settings, in spas or salons, by professional cosmetic service providers. Higher energies may be used in such settings. Even higher energies and more complex settings may be used by licensed medical professionals in medical offices.

DETAILED DESCRIPTION OF THE PREFERRED EMBODIMENTS

Figure 1:
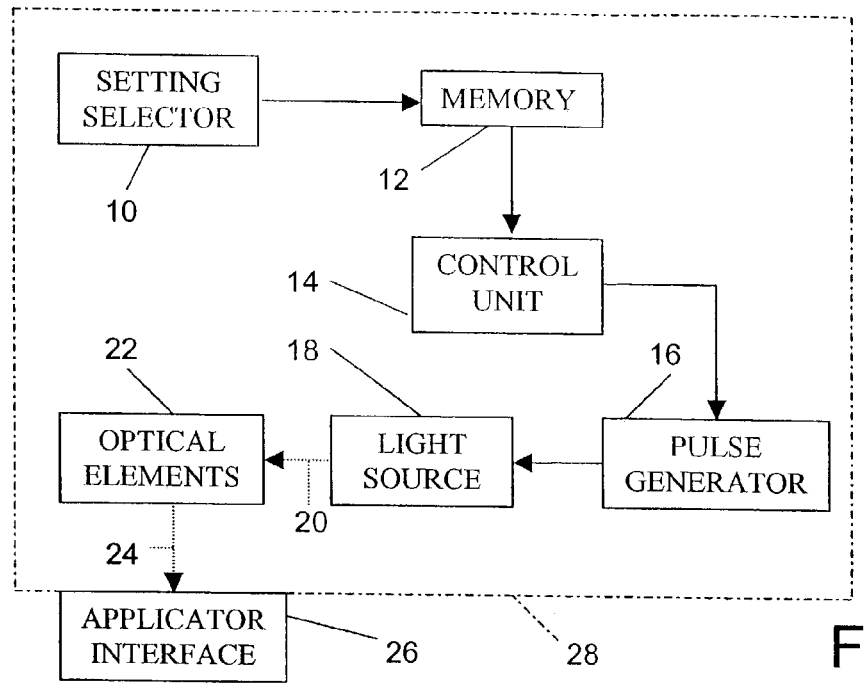
FIG. 1 is a block diagram of a light-pulse generating device for use in a method in accordance with the present invention.

As depicted in FIG. 1, a device for generating light pulses for application to a skin surface in a hair treatment process includes a manually operable setting selector 10 connected at an output to a memory 12 in turn connected at an output to a control unit 14. Memory 12 stores pre-established combinations of light pulse parameters including pulse width or duration, inter-pulse interval or delay time, pulse number, light intensity, and total treatment energy. Control unit 14 may be a microprocessor or a special logic circuit connected to a pulse generator 16 for inducing the generator to produce a sequence of electrical control pulses fed to a source 18 of incoherent light energy. Source 18 produces light with a spectral distribution including wavelengths between 500 nm and 1200 nm. Control unit 14 may be connected directly to source 18 where the source incorporates means for varying pulse parameters pursuant to encoded instructions.

Light source 18 (as well as the entire light pulse applicator) may take any known form such as those disclosed in U.S. Pat. No. 6,280,438 and U.S. Pat. No. 5,885,273. Thus, light source 18 may be a Xenon flashlamp.

Light 20 generated by source 18 is directed through an array of optical elements 22 that may include one or more reflectors, lenses, and filters (not separately shown). Where an adjustable filter is included, control unit 14 may be connected to the filter for operatively modifying the action thereof. For instance, in the case of an adjustable neutral density filter, control unit 14 may induce a change in the filter density to control the intensity, and therefore the power, of the light applied to a selected skin surface.

In the case of multiple wavelengths of light being produced, an adjustable filter may be included in the optical elements 22 and/or the applicator interface 26. These filters can block undesired wavelengths and allow desired wavelengths to pass. Low end filters that block lower or shorter wavelengths, high end filters that block higher or longer wavelengths or band pass filters that block some high or some low end wavelengths may be utilized.

Light 24 leaving the optical array 22 is delivered or applied to a skin surface via an applicator or interface element 26 exemplarily taking the form of a crystal. U.S. Pat. No. 6,280,438 and U.S. Pat. No. 5,885,273 disclose kinds of applicators or interfaces utilizable in the device of FIG. 1 (or 2). Applicator or interface element 26 may function in part to cool the skin surface prior to, during, and/or after a light application procedure. Cooling may be accomplished by using a crystal-type applicator or interface 26, with or without a layer of gel, as described in U.S. Pat. No. 6,280,438 and U.S. Pat. No. 5,885,273.

The elements of FIG. 1 are encased in or mounted to a housing 28 of a size and configuration enabling the pulse generation device to be hand held and easily manipulated for purposes of optically treating different skin surfaces of the individual user.

The device of FIG. 1 is preprogrammed to produce light pulses in any of several settings, each setting being defined by a respective combination of particular operational parameters including pulse duration, inter-pulse interval, pulse number, and intensity or total energy. For instance, the device may have a plurality of settings, for instance, high, medium, and low, which vary in the number of applied pulses (e.g., 3, 2, 1), the pulse duration (9 msec, 7 msec, 5 msec), the inter-pulse interval (250 msec, 300 msec, 350 msec), and/or the total energy applied (35 $J/cm^2$, 20 $J/cm^2$, 10 $J/cm^2$). A user could start with a low setting to see whether the hair falls out and if not, try the next higher setting. Usually, it is preferable to use the lowest setting which accomplishes the desired result.

Figure 2:
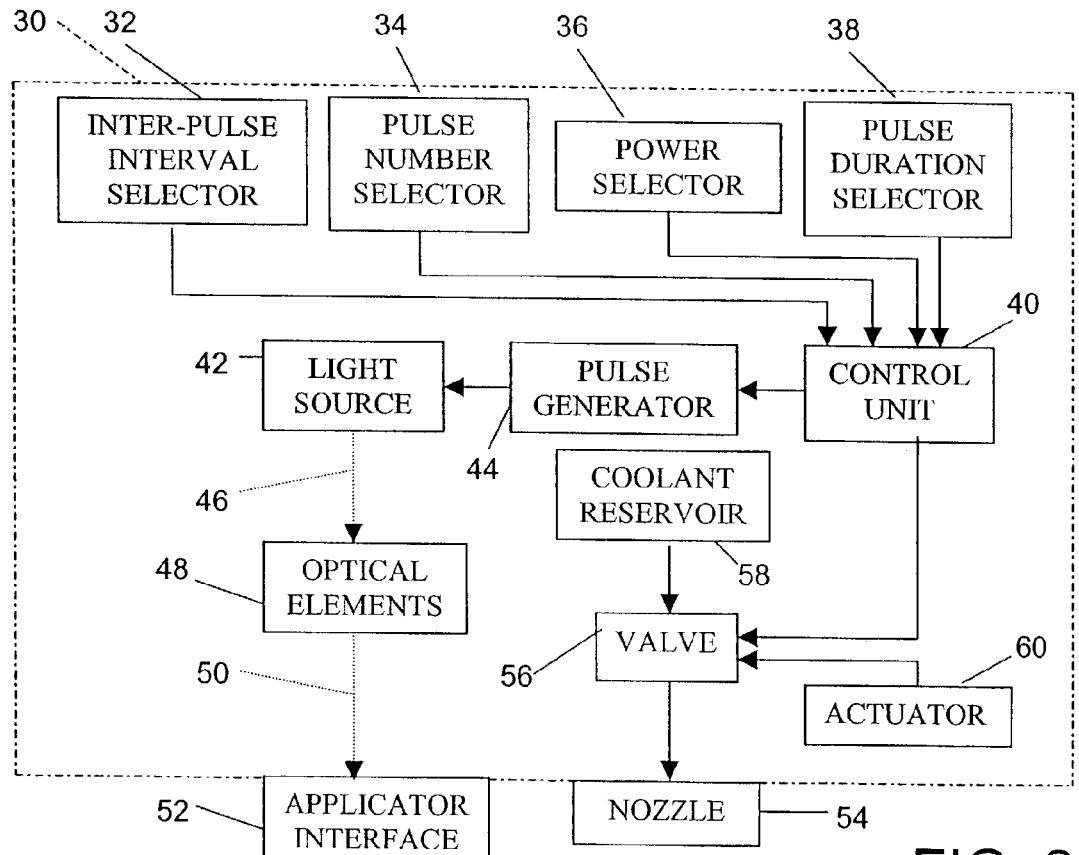
FIG. 2 is a block diagram of another light-pulse generating device for use in a method in accordance with the present invention.

A more advanced or complex device is illustrated in FIG. 2. This device includes a housing 30 having manually actuatable input elements 32, 34, 36, and 38, such as rotary knobs or a solid-state touch screen, which enable a user to individually select multiple operating parameters. Input elements or selectors 32, 34, 36, and 28 are an inter-pulse interval selector, a pulse number selector, a power or energy selector, and a pulse duration selection, respectively. Another selector (not shown) could be for intensity adjustment, while a further selector may be provided for adjusting a light source 42 or a filter in optical elements 48 and/or an applicator 52 for modifying the wavelength band delivered to the target skin surface. Selectors 32, 34, 36, and 38 are operatively tied to a control unit 40 such as a microprocessor or hard-wired log circuit. Control unit 40 regulates the operation of light source 42 such as a conventional flashlamp, either directly or indirectly via a pulse generator 44. Light 46 from source 42 is transmitted along a path through optical elements 48 optionally including one or more reflectors, lenses, and filters (not separately shown). Light 50 at an output of the optical array 48 is applied to a skin surface via applicator or interface element 52. Applicator or interface element 52 may take the form of a crystal block or a transparent or translucent pouch filled with a transparent or translucent fluid such as a gel or a liquid. In the case of a gel, the pouch (52) may be provided with perforations on a skin-contacting surface for exuding the gel of cooling purposes. Alternatively, as shown in FIG. 2, the light pulse device may be provided with a fluid dispenser such as a spray nozzle 54 connected to a valve 56 downstream of a pressurized coolant reservoir 58. In response to an operation of a manual actuator 60 or in response to signals from control unit 40, valve 56 enables a flow of coolant from reservoir 58 to nozzle 54 for application to a selected skin surface. In the event that applicator or interface element 52 is a bag or pouch, reservoir 58 and valve 56 may be connected to the applicator or interface element for supplying a gel or fluid coolant thereto.

In one embodiment of the device of FIG. 2, suitable for professional but not home use, inter-pulse interval selector 32 provides for intervals in a range from 1 msec and 2 seconds, whereas pulse number selector 34 is enabled for pulse sequences of one to ten pulses. In addition, power selector 36 permits treatment energies between 1 Joule per square centimeter of skin surface and 200 Joules per square centimeter, while pulse duration selector 38 enables pulses of 1 msec to 2 seconds in length. Total pulse sequence duration, from the beginning of the first pulse to the termination of the final pulse, ranges from 1 msec to 38 seconds. The various pulse sequence parameters may be selectable from sets of discrete values or, alternatively, from continuous ranges.

In the device of FIG. 2, the various parameters are typically not completely independent inasmuch as the total energy selected will function as a constraint on the ranges available for the other parameters, that is, the total energy selected will serve to regulate or circumscribe the ranges available to the user for the other pulse sequence parameters. Where the device of FIG. 2 has no intensity adjustment capability, a selection of the total energy and the pulse duration may determine the number of pulses. Similarly, a selection of the total energy and the number of pulses may determine the pulse duration. If the intensity is an adjustable parameter, once the total energy has been chosen, the user will be able to select the magnitudes of two of the three parameters, pulse duration, intensity and number of pulses. The inter-pulse interval is related to the rate at which radiant energy is applied to a skin surface and may accordingly be subjected to some programmed control. Longer pulse durations and/or delays will deliver energy at a slower rate (total energy is distributed over longer time) and therefore be safer to use with higher energy levels. Preferably, the total energy is always a selectable parameter and is best selected prior to the setting of the other parameters. However, the device of FIG. 2 may be preprogrammed to limit the rate at which radiant energy is applied to a skin surface, which will force restrictions on the user's ability to select pulse parameter values.

In an alternative embodiment of the device of FIG. 2, suitable for home use, inter-pulse interval selector 32 enables a selection of intervals ranging from 200 msec to 2 seconds, while power selector 36 enables treatment energies between 1 $J/cm^2$ and 40 $J/cm^2$. Preferably, the pulse duration and the number of pulses available for selection are restricted so as to prevent the user from delivering energy at too high a rate. If the user selects a large pulse number, the pulse duration is necessarily short, whereas a small number of pulses forces a longer pulse duration in order to achieve the selected total energy. It is preferable to use a larger number of pulses and a smaller pulse duration in order to limit the rate at which light energy is applied to a skin surface. Pulse number selector 34 may therefore enable a selection of three to ten pulses per pulse sequence, while pulse duration selector 38 enables a selection of pulses lasting 1 msec to 10 msec. The various pulse sequence parameters may be selectable from sets of discrete values or, alternatively, from continuous ranges.

A person uses the device of FIG. 1 or 2 to apply pulses of light to a skin surface for purposes of effectively severing or destroying hair fibers below the surface of the skin to temporarily prevent hairs from growing through and thus becoming visible on the skin. The user first performs a calibration or initialization procedure to determine an appropriate pulse setting and a hair-regeneration period for that setting. The term "hair-regeneration period" is used herein to denote the time it takes for hair to reappear on the skin surface after a pulse sequence has been applied to that surface at a selected setting.

During the calibration or initialization stage, the user should first select a low-energy pulse sequence to determine whether that sequence is effective in removing the hair of a selected skin region. The individual may find that a given setting does not adequately remove the hair (e.g., some hairs do not fall out) or requires a too frequent treatment. In such cases, the individual should retry the calibration or initialization procedure using a higher-energy setting.

Using the device of FIG. 1, an individual will first select a low setting to determine whether that low setting is effective in hair removal. If not, a next higher or medium setting may be tried. Generally, higher settings will be used only as the circumstances warrant, for instance, if the hair fibers are thick and the skin is light.

In determining optimal settings with the device of FIG. 2, a user should choose initial parameter values which in combination result in the application of small amounts of energy. Thus, where one or more selected pulse parameters are associated with high treatment energies, other pulse parameters should be selected that are associated with low treatment energies.

Where all the pulse parameters are independently adjustable, lower treatment energies will generally result from settings involving few pulses (say, 1–3 instead of 8–10 pulses), long inter-pulse intervals (300 msec or more), short pulse durations (20 msec or less), low light intensity (if selectable, for example, via an adjustable neutral density filter), and low total energies (less than 40 Joules per square centimeter of skin surface). If a given setting proves to be ineffective, the user might adjust selector 32 or 38 to decrease the inter-pulse interval or increase the pulse length, thereby effectively increasing the power or rate at which the radiant energy is delivered to the target skin surface. Alternatively or additionally, the user might increase the number of pulses via selector 34 or increase the applied energy via selector 36. These adjustments will result in an increase in the rate of applied energy if the total time of the pulse sequence is limited. If the light intensity is separately adjustable, one may increase the power or rate of energy delivery by simply selecting a higher intensity value.

Where the various pulse parameters are not independently selectable, for instance, where the total energy applied is a controlling factor, adjustments made in the parameters for purposes of incrementally enhancing the hair removal effectiveness of the device of FIG. 2 will be different from the case of completely independent parameter values. For instance, once the total applied energy and total pulse sequence time have been selected, decreasing the number of pulses will require an increase in pulse length and/or an increase in pulse intensity in order to deliver the same amount of total energy in the fixed time. These changes will increase the effectiveness of the light application inasmuch as the rate of energy delivery is increased. In contrast, once the total applied energy and total pulse sequence time have been selected, increasing the pulse duration will decrease the instantaneous rate at which energy is applied to the target skin surface by decreasing the light intensity,.

During the calibration or initialization stage of a hair removal method using the device of FIG. 1 or FIG. 2, light is used on skin surfaces with visible and protruding hair. Light is applied to the skin surface and the hair and is directed downward towards the base or bulb of the hair. Immediate damage to the hair may be noted but is not essential. Hairs may fall out during the course of the following month. Hair loss may be gradual or abrupt. No assistance is usually needed in this process.

Since hair growth rates vary from person to person and for different body locations on the same person, each user should note the interval between the first treatment and the reappearance of new hair on each skin area.

Because different skin areas have different grades of hair (different colors, different fiber diameters, different hair densities) and different skin pigmentation, etc., different pulse parameter settings are recommended for different skin areas. For example, different settings will be necessary for the underarms and the legs in order to optimize results. In addition, depilation schedules may also vary from one skin area to another.

After the user has determined appropriate settings of the pulse sequence parameters and expected hair-regeneration periods for different skin areas, the user then treats each skin surface with pulsed light at the respective setting and at a periodicity set by the respective hair-regeneration period. Successive applications of pulsed light follow at intervals smaller than the detected hair-regeneration period. For instance, if it is determined that hair reappears on a leg at three weeks after treatment with light at a given pulse sequence setting, then light energy at that setting is applied to the leg at, say, two week intervals to maintain the leg free of visible hair. The regeneration period may be measured again after any number of treatments. And if the user finds that the regeneration time has changed, the interval between successive treatment sessions may be adjusted accordingly.

This hair removal method contemplates, therefore, the periodic application to a selected skin surface of a pulse sequence having a predetermined number of pulses of light of a predetermined electromagnetic spectrum, a predetermined duration, a predetermined inter-pulse interval, and a predetermined total energy. These pulse sequence parameters are determined in part by the design of the light generating device used and in part by the selections made by the user. The light treatment temporarily prevents a growth of hair through the selected skin surface for the respective hair-regeneration period. The delay in the reappearance of hair on the selected skin surface after a first application of light pulses may be extended simply by applying light pulses again to the skin surface prior to hair reappearance on the skin surface.

The light of the pulses is generally incoherent and the spectrum includes wavelengths between about 300 nm and 1200 nm. However, single wavelengths of laser or coherent light may be delivered at one time, when desired. Higher wavelengths are used for darker skin, for deeper hairs and deeper removal. In order to limit the depth of penetration of the light, and accordingly the length of the hair-regeneration or hair-regrowth period, the spectrum of the pulses may be limited to shorter wavelengths and may include wavelengths, for instance, below 550 nm.

In other embodiments of a light generation and application device, one or more of the pulse parameters may vary during a single treatment session. For instance, the inter-pulse interval or the pulse duration may increase or decrease from the beginning of a pulse sequence to the end of the pulse sequence. The resulting instantaneous rate of energy application may therefore vary during the pulse sequence.

Listed below are a number of exemplary settings or combinations of operational parameters particularly suitable for home-use and attainable with either the device of FIG. 1 having pre-established settings or parameter combinations or the device of FIG. 2 where the various pulse sequence parameters may be individually adjusted independently of the other parameters. In these examples, the total times of the pulse sequences are determined by the selected numbers of pulses, the selected pulse durations and the selected inter-pulse intervals. The light intensity may be automatically adjusted by the light generating device if necessary to ensure consistency among the listed parameter settings.

Home Use Example 1. In a preferred setting or combination of operational parameters suitable for home use, an incoherent light applicator device for temporary hair removal generates pulses with a pulse number of two, a pulse duration of 7 msec, an inter-pulse interval of 300 msec, a total pulse energy of 20 J/cm$^2$, and a spectral distribution of a commercially available flashlamp, including wavelengths between 500 and 1200 nm.

Home Use Example 2. A slightly higher setting or combination of operational parameters for an incoherent light applicator device suitable for home use involves a pulse sequence with a pulse number of two, a pulse duration of 7 msec, an inter-pulse interval of 250 msec, a total pulse energy of 20 J/cm$^2$, and a spectral distribution of a commercially available flashlamp, including wavelengths between 500 and 1200 nm. Although the total amount of energy is the same as in the first example, the shorter interpulse interval means that the rate of energy transmission to the target skin surface is higher.

Home Use Example 3. A higher setting or combination of operational parameters for an incoherent light applicator device involves pulses with a pulse number of two, a pulse duration of 5 msec, an inter-pulse interval of 250 msec, a total pulse energy of 25 J/cm$^2$, and a spectral distribution of a commercially available flashlamp, including wavelengths between 500 and 1200 nm. In this example, not only is the total energy larger than in the second example, but the rate of energy application is higher owing to the shorter pulse duration.

Home Use Example 4. An even higher setting or combination of operational parameters for an incoherent light applicator device involves pulses with a pulse number of two, a pulse duration of 5 msec, an inter-pulse interval of 210 msec, a total pulse energy of 37 J/cm$^2$, and a spectral distribution of a commercially available flashlamp, including wavelengths between 500 and 1200 nm. The pulse sequence of this example delivers radiant energy at a higher rate than in the third example because of the shorter inter-pulse interval and the slightly higher energy delivered per pulse.

Home Use Example 5. In a low setting or combination of operational parameters, an incoherent light applicator device produces pulses with a pulse number of two, a pulse duration of 5 msec, an inter-pulse interval of 350 msec, a total pulse energy of 15 J/cm$^2$, and a spectral distribution of a commercially available flashlamp, including wavelengths between 500 and 1200 nm. The pulse sequence of this example delivers a small amount of energy, at a low rate (e.g., long inter-pulse interval).

Home Use Example 6. A slightly higher setting or combination of operational parameters for an incoherent light applicator device involves pulses with a pulse number of two, a pulse duration of 5 msec, an inter-pulse interval of 300 msec, a total pulse energy of 20 J/cm$^2$, and a spectral distribution of a commercially available flashlamp, including wavelengths between 500 and 1200 nm.

Home Use Example 7. A lower setting or combination of operational parameters for an incoherent light applicator device involves pulses with a pulse number of three, a pulse duration of 5 msec, an inter-pulse interval of 300 msec, a total pulse energy of 20 J/cm$^2$, and a spectral distribution of a commercially available flashlamp, including wavelengths between 500 and 1200 nm.

Home Use Example 8. Another setting or combination of operational parameters for an incoherent light applicator device involves pulses with a pulse number of two, a pulse duration of 7 msec, an inter-pulse interval of 250 msec, a total pulse energy of 20 J/cm$^2$, and a spectral distribution of a commercially available flashlamp, including wavelengths between 500 and 1200 nm.

The devices of FIGS. 1 and 2 may be provided with a band-pass filter for limiting the spectral distribution of the generated light pulses to wavelengths in a given band, for instance, between 700 nm and 900 nm. Alternatively, a low-pass filter may be used for transmitting to a skin surface only wavelengths less than a predetermined maximum, such as 900 nm, 750 nm, or 550 nm. The lower the wavelength the less likely the light will penetrate deeply and damage cellular and histological elements as deep as the bulb parts of the hair follicles. Shorter wavelengths, for instance, below 550 nm are useful for limiting the depth of penetration. It is to be understood, however, that the less the depth of penetration, the shorter the time between successive applications of light energy necessary to maintain a hair free skin surface. Thus, instead of a month or a week, the time between successive hair removal procedures might be as little as one or two days.

Depth of penetration may also be limited by using lower light intensities. Neutral density or "gray" filters may be used to reduce the intensity of the light applied to the selected skin surfaces.

Listed below are a number of exemplary settings or combinations of operational parameters particularly suitable for professional devices. In these examples, the total times of the pulse sequences are determined by the selected numbers of pulses, the selected pulse durations and the selected inter-pulse intervals. The light intensity may be automatically adjusted by the light generating device if necessary to ensure consistency among the listed parameter settings.

Professional Use Example 1. In a setting or combination of operational parameters suitable for professional use, an incoherent light applicator device for temporary hair removal generates pulses with a pulse number of two, a pulse duration of 7 msec, an inter-pulse interval of 150 msec, a total pulse energy of 60 J/cm$^2$, and a spectral distribution of a commercially available flashlamp, including wavelengths between 500 and 1200 nm.

Professional Use Example 2. A slightly higher setting or combination of operational parameters for an incoherent light applicator device involves pulses with a pulse number of two, a pulse duration of 7 msec, an inter-pulse interval of 100 msec, a total pulse energy of 60 J/cm$^2$, and a spectral distribution of a commercially available flashlamp, including wavelengths between 500 and 1200 nm.

Professional Use Example 3. A lower setting or combination of operational parameters for an incoherent light applicator device involves pulses with a pulse number of two, a pulse duration of 9 msec, an inter-pulse interval of 100 msec, a total pulse energy of 60 J/cm$^2$, and a spectral distribution of a commercially available flashlamp, including wavelengths between 500 and 1200 nm.

Professional Use Example 4. A higher setting or combination of operational parameters for an incoherent light applicator device involves pulses with a pulse number of two, a pulse duration of 9 msec, an inter-pulse interval of 100 msec, a total pulse energy of 100 J/cm$^2$, and a spectral distribution of a commercially available flashlamp, including wavelengths between 500 and 1200 nm.

Professional Use Example 5. In a relatively low setting or combination of operational parameters for professional use, an incoherent light applicator device produces pulses with a pulse number of two, a pulse duration of 9 msec, an inter-pulse interval of 200 msec, a total pulse energy of 40 J/cm$^2$, and a spectral distribution of a commercially available flashlamp, including wavelengths between 500 and 1200 nm.

Professional Use Example 6. A slightly higher setting or combination of operational parameters for an incoherent light applicator device involves pulses with a pulse number of two, a pulse duration of 5 msec, an inter-pulse interval of 150 msec, a total pulse energy of 40 J/cm$^2$, and a spectral distribution of a commercially available flashlamp, including wavelengths between 500 and 1200 nm.

Professional Use Example 7. Another higher setting or combination of operational parameters for an incoherent light applicator device involves pulses with a pulse number of two, a pulse duration of 5 msec, an inter-pulse interval of 150 msec, a total pulse energy of 50 J/cm$^2$, and a spectral distribution of a commercially available flashlamp, including wavelengths between 500 and 1200 nm.

An incoherent light applicator device for professional use may also be provided with a band-pass filter for limiting the spectral distribution of the generated light pulses to wavelengths in a given band, for instance, between 700 nm and 900 nm. Again, a low-pass filter may be used for transmitting to a skin surface only wavelengths less than a predetermined maximum, such as 900 nm, 750 nm, or 550 nm.

The hair treatment method described above with reference to FIGS. 1 and 2 results not only in a temporary hair removal at an optically treated skin surface, but also retards the growth of hair fibers located at or along that skin surface. By counting the days to hair reappearance after several hair depilation procedures over a course of a few months, it is possible to determine a reduction in hair growth rate owing to the application of electromagnetic radiation. A user who starts using the light application process at one inter-application interval may subsequently use a longer inter-application interval and still maintain a hair-free skin surface. Of course, the degree of hair growth rate reduction will vary from person to person and even from skin location to skin location on the same person. For example, two users initially required to apply the pulsed light energy at intervals of one week in order to prevent the reappearance of hair on the treated hair surface may find that after several months one user need reapply light energy only every two weeks and the other user need reapply light energy only every month.

It is to be noted that the hair treatment method described herein contemplates multiple passes over any particular skin surface. The selected light treatment parameters may be the same for each pass or may vary from pass to pass. In addition, the passes may follow immediately after one another or may be spaced by an interval during which, for instance, the light treatment device is used to apply light pulses to another area of the user's skin. An advantage of multiple passes is that the total power applied to a given skin surface may be reduced relative to that needed for accomplishing the desired hair removal by a single pass or light treatment. For example, instead of a single pass of 50 Joules/cm$^2$, hair could be effectively removed temporarily by two passes of 20 Joules/cm$^2$ apiece.

Although the invention has been described in terms of particular embodiments and applications, one of ordinary skill in the art, in light of this teaching, can generate additional embodiments and modifications without departing from the spirit of or exceeding the scope of the claimed invention. For example, light sources 18 and 42 may take the form of laser sources. In that case, if optical elements 22 and 48 include any filters, those filters are neutral density filters for reducing the intensity of the transmitted radiation. Where light sources 18 and 42 are tunable laser sources, then an additional actuator may be provided for frequency selection purposes. Accordingly, it is to be understood that the drawings and descriptions herein are proffered by way of example to facilitate comprehension of the invention and should not be construed to limit the scope thereof.

What is claimed:

1. A hair treatment method for at least temporarily slowing hair growth along a skin surface, comprising:
    generating a predetermined number of pulses of light each having a predetermined electromagnetic spectrum;
    directing said pulses of light towards a skin surface, said pulses having at least one pulse duration, and a total energy all predetermined to at least temporarily retard growth of hair along said skin surface, the directing of said pulses towards said skin surface being undertaken in the absence of visible hair on said skin surface to delay an appearance of hair on said skin surface; and
    after lapse of a substantial period of time after the directing of said pulses towards said skin surface and prior to a visible appearance of hair on said skin surface, again generating pulses of light and directing the pulses towards said skin surface to further delay an appearance of hair on said skin surface.

2. The method defined in claim 1 wherein said number of pulses is greater than one, said pulses having an inter-pulse interval greater than 200 msec.

3. The method defined in claim 2 wherein said total energy is between approximately 1 Joule and approximately 200 Joules of energy per square centimeter of said skin surface.

4. The method defined in claim 3 wherein said duration is between approximately 1 msec and approximately 2 seconds.

5. The method defined in claim 4 wherein the light of said pulses is incoherent and wherein said spectrum includes wavelengths between about 300 nm and 1200 nm.

6. The method defined in claim 5 wherein said spectrum includes only wavelengths between about 300 nm and about 550 nm.

7. The method defined in claim 4 wherein said duration is between approximately 1 msec and approximately 20 msec.

8. The method defined in claim 3 wherein said total energy is between approximately 5 Joules and approximately 40 Joules of energy per square centimeter of said skin surface.

9. The method defined in claim 1 wherein said period of time has a length between a day and nine months.

10. A hair treatment method comprising:
generating a predetermined number of pulses of light each having a predetermined electromagnetic spectrum;
applying said pulses of light to a skin surface, said pulses having at least one predetermined pulse duration, and a predetermined total energy;
at least in part owing to the applying of said pulses to said skin surface, temporarily preventing an appearance of hair fibers on said skin surface;
counting days between the applying of said pulses to said skin surface and a subsequent reappearance of hair fibers on said skin surface to determine a first lapsed period of time;
after determining of said period of time, generating additional pulses of light of said predetermined number and having said spectrum;
directing said additional pulses of light towards said skin surface, said additional pulses having said duration, and said total energy;
counting days between the directing of said additional pulses towards said skin surface and a subsequent reappearance of hair fibers on said skin surface to determine a second lapsed period of time longer than said first lapsed period of time;
after determining of said period of time, generating supplemental pulses of light of said predetermined number and having said spectrum;
directing said supplemental pulses of light towards said skin surface, said supplemental pulses having said duration, and said total energy;
prior to a lapse of said second lapsed period of time after the directing of said supplemental pulses towards said skin surface, generating further pulses of light of said predetermined number and having said spectrum; and
directing said further pulses of light towards said skin surface, said further pulses having said duration, and said total energy.

11. The method defined in claim 10 wherein said number of pulses is greater than one, said pulses having an inter-pulse interval between 1 msec and 2 seconds.

12. The method defined in claim 11 wherein said inter-pulse interval is greater than 200 msec.

13. The method defined in claim 10 wherein said total energy is between approximately 1 Joule and approximately 200 Joules of energy per square centimeter of said skin surface.

14. The method defined in claim 10 wherein said duration is between approximately 1 msec and approximately 2 seconds.

15. The method defined in claim 10 wherein the light of said pulses is incoherent and wherein said spectrum includes wavelengths between about 300 nm and 1200 nm.

16. The method defined in claim 15 wherein said spectrum includes wavelengths between about 300 nm and about 550 nm only.

17. The method defined in claim 10 wherein said second lapsed period of time has a length between a day and nine months.

18. A hair treatment method comprising:
generating a predetermined number of pulses of light each having a predetermined electromagnetic spectrum including one or more wavelengths absorbable by hair fibers;
applying said pulses of light to a skin surface, said pulses having at least one predetermined pulse duration, and a predetermined total energy all predetermined to effectively sever or destroy hair fibers below said skin surface;
by virtue of an absorption of light of said pulses by hair fibers below said skin surface, at least temporarily retarding hair growth along said skin surface; and
subsequently repeatedly applying pulses of light to said selected skin surface at intervals of increasing length owing to a diminution in a growth rate of hair along said skin surface.

19. The method defined in claim 18 wherein said number of pulses is greater than one, said pulses having an inter-pulse interval between 1 msec and 2 seconds.

20. The method defined in claim 18 wherein said total energy is between approximately 1 Joule and approximately 200 Joules of energy per square centimeter of said skin surface.

21. The method defined in claim 20 wherein said duration is between approximately 1 msec and approximately 2 seconds.

22. The method defined in claim 21 wherein the light of said pulses is incoherent and wherein said spectrum includes wavelengths between about 300 nm and 550 nm only.

23. A hair treatment method comprising:
generating a predetermined number of first pulses of light each having a predetermined electromagnetic spectrum;
directing said first pulses of light towards a skin surface,
after lapse of a period of time after the directing of said first pulses towards said skin surface, generating a predetermined number of second pulses of light each having a predetermined electromagnetic spectrum; and
directing said second pulses of light towards said skin surface,
said first pulses having at least one pulse duration and a total energy and said second pulses having at least one pulse duration and a total energy, all predetermined to reduce hair appearance along said skin surface,
said period of time being sufficiently small so that the directing of said first pulses and the directing of said second pulses constitute respective passes over said skin surface in a single light treatment sessions,
wherein said skin surface is on an individual user, further comprising applying light pulses to another skin surface of said individual user during said period.

24. The method defined in claim 23 wherein said first pulses of light and said second pulses of light are defined by respective sets of parameters including pulse duration and total energy, the parameters of said first pulses of light being the same as the parameters of said second pulses of light.

25. A method for hair removal and temporarily preventing hair reappearance, comprising:
generating a predetermined number of pulses of light each having a predetermined electromagnetic spectrum;
directing said pulses of light towards a skin surface, said pulses having at least one pulse duration, and a total energy all predetermined to temporarily prevent a growth of hair through said skin surface for a period of time;
effectuating a removal of projecting hair fibers from said skin surface;
determining said period of time for hair to reappear on said skin surface after the directing of said pulses of light to said skin surface; and
prior to a lapse of said period of time after the directing of said pulses towards said skin surface, after the removal of projecting hair from said skin surface, and prior to a visible reappearance of hairs on said skin surface, again generating pulses of light and directing the pulses towards said skin surface.

26. A method for hair removal and temporarily preventing hair reappearance, comprising:

providing a device for generating a predetermined number of pulses of light each having a predetermined electromagnetic spectrum and for applying said pulses of light to a skin surface, said pulses having at least one predetermined pulse duration, and a predetermined total energy;

using said device to temporarily remove hair from a selected skin surface;

determining a period of time for reappearance of hair on said selected skin surface after the using of said device; and subsequently repeatedly using said device to apply pulses of light to said selected skin surface at intervals of shorter length than said period of time, each such use of said device to apply pulses of light to said selected skin surface being performed prior to a visible reappearance of hair on said selected skin surface, thereby temporarily maintaining said selected skin surface free of visible hair.

27. A method for hair removal and temporarily preventing hair reappearance, comprising:

generating a predetermined number of pulses of light each having a predetermined electromagnetic spectrum;

directing said pulses of light towards a skin surface, said pulses having at least one pulse duration, and a total energy all predetermined to effectively sever or destroy hair fibers below said skin surface, thereby enabling a removal of projecting hair fibers from said skin surface, and to temporarily prevent a growth of hair through said skin surface for a period of time;

determining said period of time for hair to reappear on said skin surface after the directing of said pulses of light to effectively sever or destroy hair fibers below said skin surface; and prior to a lapse of said period of time and concomitantly prior to a visible appearance of hairs on said skin surface after the directing of said pulses towards said skin surface, again generating pulses of light and directing the pulses towards said skin surface, thereby temporarily maintaining said skin surface free of visible hair.

28. A hair treatment method comprising:

generating a predetermined number of pulses of light each having a predetermined electromagnetic spectrum;

directing said pulses of light towards a skin surface, said pulses having at least one pulse duration, and a total energy all predetermined to change at least one hair characteristic taken from the group consisting of thickness, density and color, the directing of said pulses towards said skin surface being undertaken in the absence of visible hair on said skin surface; and after lapse of a substantial period of time after the directing of said pulses towards said skin surface and prior to a visible appearance of hair on said skin surface, again generating pulses of light and directing the pulses towards said skin surface to further change at least one hair characteristic taken from the group consisting of thickness, density and color.

29. A hair treatment method comprising:

generating a predetermined number of pulses of light each having an electromagnetic spectrum including one or more wavelengths absorbable by hair fibers;

directing said pulses of light towards a skin surface, said pulses having at least one pulse duration, and a total energy all predetermined to at least temporarily retard growth of hair along said skin surface;

by virtue of the directing of said pulses of light towards said skin surface and absorption of light of said pulses by hair fibers below said skin surface, effectuating a removal of projecting hair fibers from said skin surface;

also by virtue of the directing of said pulses of light towards said skin surface and absorption of light of said pulses by hair fibers below said skin surface, retarding the growth of hair along said skin surface, while permitting the hair to continue growing; and after lapse of a period of time after the directing of said pulses towards said skin surface, again generating pulses of light and directing the pulses towards said skin surface to thereby further retard but not terminate the growth of the hair along said skin surface.

30. A hair treatment method comprising:

generating a predetermined number of pulses of light each having an electromagnetic spectrum;

directing said pulses of light towards a skin surface during a first treatment session so that light of said pulses is absorbed by hair fibers at points below said skin surface and change a characteristic of the absorbing fibers while permitting the absorbing hair fibers to continue growing;

removing, from said skin surface, projecting portions of the hair fibers that absorb light of said pulses;

after lapse of a substantial period of time after the directing of said pulses towards said skin surface and after removal of the projecting portions of the hair fibers, generating additional pulses of light and directing the additional pulses towards said skin surface in a second treatment session so that light of said additional pulses is absorbed by hair fibers at points below said skin surface and change a characteristic of the absorbing fibers while permitting the absorbing hair fibers to continue growing; and after regrowth of the hair fibers whose projecting portions were removed from said skin surface, the regrown hair fibers again having projecting portions above said skin surface, removing, from said skin surface, such projecting portions of the hair fibers absorbing the light of said additional pulses.

31. A method for hair treatment, comprising:

generating a predetermined number of pulses of light each having a predetermined electromagnetic spectrum including one or more wavelengths absorbable by hair fibers;

directing said pulses of light towards a skin surface, said pulses having at least one pulse duration and a total energy all predetermined to effectively sever or destroy hair fibers below said skin surface; and by virtue of the directing of said pulses of light towards said skin surface and absorption of light of said pulses by hair fibers below said skin surface, severing or damaging the hair fibers below said skin surface to delay a growth of hair through said skin surface.

32. A method for hair treatment, comprising:

generating a predetermined number of pulses of light each having a predetermined electromagnetic spectrum with one or more wavelengths absorbable by hair;

directing said pulses of light towards a skin surface, said pulses having at least one pulse duration and a total energy all predetermined to effectively vary a characteristic of hair fibers along said skin surface owing to absorption of light of said pulses by the hair fibers; and by virtue of the directing of said pulses of light towards said skin surface and absorption of light of said pulses by hair fibers along and below said skin surface, changing a characteristic of hair fibers along said skin surface.

* * * * *

(12) EX PARTE REEXAMINATION CERTIFICATE (7422nd)
United States Patent
Jay

(10) Number: US 7,175,617 C1
(45) Certificate Issued: Mar. 23, 2010

(54) HAIR TREATMENT METHOD

(76) Inventor: Harvey H. Jay, 14 Cayuga Rd., Scarsdale, NY (US) 10583

Reexamination Request:
No. 90/010,254, Aug. 26, 2008

Reexamination Certificate for:
Patent No.: 7,175,617
Issued: Feb. 13, 2007
Appl. No.: 10/418,604
Filed: Apr. 18, 2003

Related U.S. Application Data

(63) Continuation-in-part of application No. 10/291,086, filed on Nov. 8, 2002, now Pat. No. 6,824,542.

(51) Int. Cl.
*A61B 18/18* (2006.01)

(52) U.S. Cl. ............ 606/9; 606/10; 606/3; 607/88; 128/898

(58) Field of Classification Search ............ None
See application file for complete search history.

(56) References Cited

U.S. PATENT DOCUMENTS 5,683,380 A  11/1997  Eckhouse et al. ............ 606/9

7,044,959 B2  5/2006  Anderson et al.
2004/0034319 A1  2/2004  Anderson et al.

OTHER PUBLICATIONS

U.S. Appl. No. 60/363,871, filed Mar. 12, 2002, Anderson et al.

"Effects of Fluence and Pulse Duration for Flashlamp Exposure on Hair Follicles," presented at the 21st Annual Meeting for the American Society for Laser Medicine & Surgery, Apr. 2001 ("Manstein").

*Primary Examiner*—David O. Reip

(57) ABSTRACT

A hand held device generates a predetermined number of pulses of light having a predetermined electromagnetic spectrum, a predetermined duration, a predetermined interpulse interval, and a predetermined total energy. The pulse sequence is delivered to a skin surface to temporarily remove hair. A period of time for reappearance of hair on the selected skin surface after the using of the device to remove hair from the selected skin surface is determined by counting the days to hair reappearance after a test light application. Subsequently, the device is used periodically to apply the pulses of light to the selected skin surface at intervals of shorter length than the determined period of hair regeneration, thereby temporarily maintaining the selected skin surface free of visible hair.

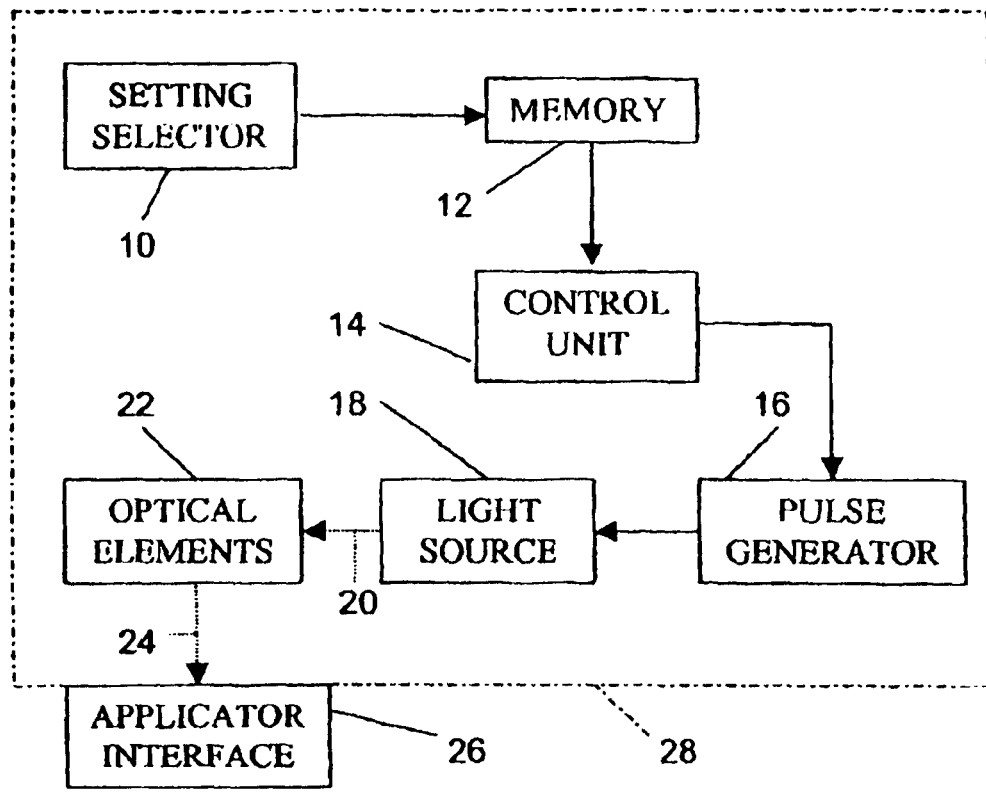

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 18–21 and 31 is confirmed.

Claim 32 is cancelled.

New claims 33–36 are added and determined to be patentable.

Claims 1–17 and 22–30 were not reexamined.

*33. A hair treatment method comprising: generating a predetermined number of pulses of light each having a predetermined electromagnetic spectrum including one or more wavelengths absorbable by hair fibers; applying said pulses of light to a skin surface, said pulses having at least one predetermined pulse duration, and a predetermined total energy all predetermined to effectively sever or destroy hair fibers below said skin surface without partially or completely destroying follicles associated with such hair fibers; by virtue of an absorption of light of said pulses by hair fibers below said skin surface so as to sever such hair fibers below said skin surface without partially or completely destroying follicles associated with such hair fibers, at least temporarily retarding hair appearance along said skin surface; and subsequently repeatedly applying pulses of light to said selected skin surface at intervals of increasing length owing to diminution in a reappearance rate of hair along said skin surface.*

*34. A method for hair treatment, comprising: generating a predetermined number of pulses of light each having a predetermined electromagnetic spectrum including one or more wavelengths absorbable by hair fibers; directing said pulses of light towards a skin surface, said pulses having at least one pulse duration and a total energy all predetermined to effectively sever or destroy hair fibers below said skin surface without partially or completely destroying follicles associated with said hair fibers; and by virtue of the directing of said pulses of light towards said skin surface and absorption of light of said pulses by hair fibers below said skin surface, severing or damaging the hair fibers below said skin surface, without partially or completely destroying follicles associated with such hair fibers, to delay a reappearance of hair through said skin surface.*

*35. A hair treatment method comprising: generating a predetermined number of pulses of light each having a predetermined electromagnetic spectrum including one or more wavelengths absorbable by hair fibers; applying said pulses of light to a skin surface, said pulses having at least one predetermined pulse duration, and a predetermined total energy all predetermined to effectively sever or destroy hair fibers below said skin surface; by virtue of an absorption of light of said pulses by hair fibers below said skin surface, at least temporarily retarding hair growth along said skin surface; and subsequently repeatedly applying pulses of light to said selected skin surface at intervals of increasing length owing to a diminution in a growth rate of hair along said skin surface, the reapplying of pulses of light being undertaken prior to reappearance of hair on said skin surface.*

*36. A method for hair treatment, comprising: generating a predetermined number of pulses of light each having a predetermined electromagnetic spectrum including one or more wavelengths absorbable by hair fibers; directing said pulses of light towards a skin surface, said pulses having at least one pulse duration and a total energy all predetermined to effectively sever or destroy hair fibers below said skin surface; and by virtue of the directing of said pulses of light towards said skin surface and absorption of light of said pulses by hair fibers below said skin surface, severing or damaging the hair fibers below said skin surface, to delay a growth of hair through said skin surface, further comprising subsequently redirecting pulses of light to said skin surface prior to reappearance of hair on or regrowth of hair through said skin surface.*

\* \* \* \* \*